(12) United States Patent
Link et al.

(10) Patent No.: US 8,845,751 B2
(45) Date of Patent: Sep. 30, 2014

(54) ENDOPROSTHESIS COMPONENT

(75) Inventors: Helmut D. Link, Hamburg (DE); Roger Thull, Würzburg (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 143 days.

(21) Appl. No.: 12/235,356

(22) Filed: Sep. 22, 2008

(65) Prior Publication Data
US 2009/0082866 A1    Mar. 26, 2009

Related U.S. Application Data

(60) Provisional application No. 60/974,303, filed on Sep. 21, 2007.

(51) Int. Cl.
```
A61F 2/28      (2006.01)
A61L 33/00     (2006.01)
B05D 3/00      (2006.01)
A61F 2/36      (2006.01)
A61F 2/30      (2006.01)
A61F 2/38      (2006.01)
```

(52) U.S. Cl.
CPC ..... *A61F 2/30767* (2013.01); *A61F 2310/0055* (2013.01); *A61F 2/3607* (2013.01); *A61F 2002/30677* (2013.01); *A61F 2310/00544* (2013.01); *A61F 2/28* (2013.01); *A61F 2310/00485* (2013.01); *A61F 2310/00407* (2013.01); *A61F 2002/3092* (2013.01); *A61F 2310/0052* (2013.01); *A61F 2002/30929* (2013.01); *A61F 2/38* (2013.01); *A61F 2220/0025* (2013.01); *A61F 2310/00491* (2013.01); *A61F 2310/00538* (2013.01); *A61F 2310/00443* (2013.01); *A61F 2310/00568* (2013.01); *A61F 2310/00449* (2013.01); *A61F 2002/2825* (2013.01); *A61F 2310/00467* (2013.01); *A61F 2/3094* (2013.01); *A61F 2002/30405* (2013.01); *A61F 2310/00856* (2013.01)
USPC ............ 623/23.6; 427/2.24; 623/1.46

(58) Field of Classification Search
USPC ................. 623/1.46, 23.6; 427/2.24
See application file for complete search history.

(56) References Cited

U.S. PATENT DOCUMENTS

| | | | |
|---|---|---|---|
| 4,693,760 A | 9/1987 | Sioshansi | |
| 6,080,490 A * | 6/2000 | Burrell et al. | 428/461 |
| 6,245,104 B1 * | 6/2001 | Alt | 427/2.25 |
| 6,953,560 B1 * | 10/2005 | Castro et al. | 423/423 |
| 7,371,425 B2 * | 5/2008 | Rathenow et al. | 427/2.24 |

(Continued)

FOREIGN PATENT DOCUMENTS

| | | |
|---|---|---|
| CN | 1231591 | 10/1999 |
| CN | 1638820 | 7/2005 |

(Continued)

*Primary Examiner* — Randy Shay
(74) *Attorney, Agent, or Firm* — Morrison & Foerster LLP

(57) ABSTRACT

An endoprosthesis component and a method for producing an endoprosthesis component is disclosed. The endoprosthesis component comprises a body predefining the shape of the endoprosthesis component. On surface portions with which the endoprosthesis component in the implanted state is in contact with human tissue, the body is covered with an outer layer which comprises a nitride, an oxynitride or an oxide based on a refractory metal and which contains silver and/or copper. An intermediate layer is arranged between the outer layer and the body in such a way that parts of the intermediate layer are accessible from the outside. The endoprosthesis component enables generation of a long-term antimicrobial action with the outer layer and, in addition, action on the surrounding tissue from the intermediate layer.

14 Claims, 3 Drawing Sheets

(56) References Cited

U.S. PATENT DOCUMENTS

| | | | |
|---|---|---|---|
| 7,709,045 B2* | 5/2010 | Flanagan | 427/2.1 |
| 2005/0055014 A1* | 3/2005 | Coppeta et al. | 604/890.1 |
| 2005/0070989 A1* | 3/2005 | Lye et al. | 623/1.4 |
| 2005/0079200 A1* | 4/2005 | Rathenow et al. | 424/423 |
| 2005/0079201 A1* | 4/2005 | Rathenow et al. | 424/424 |
| 2006/0161256 A1* | 7/2006 | Ziegler et al. | 623/11.11 |
| 2006/0167147 A1* | 7/2006 | Asgari | 524/174 |
| 2006/0194008 A1* | 8/2006 | Schwartz et al. | 428/34.4 |
| 2006/0211802 A1* | 9/2006 | Asgari | 524/439 |
| 2006/0241747 A1* | 10/2006 | Shaoulian et al. | 623/2.37 |
| 2007/0003753 A1* | 1/2007 | Asgari | 428/315.5 |

FOREIGN PATENT DOCUMENTS

| | | |
|---|---|---|
| JP | 2005-137801 | 6/2005 |
| JP | 2007-181705 | 7/2007 |
| WO | WO-98/14139 | 4/1998 |
| WO | WO-03/049781 | 6/2003 |
| WO | WO-03/094774 A1 | 11/2003 |
| WO | WO-2006/004645 | 1/2006 |

* cited by examiner

ENDOPROSTHESIS COMPONENT

CROSS REFERENCE TO RELATED APPLICATION

This application claims priority to U.S. Provisional Application No. 60/974,303 filed Sep. 21, 2007, the entire contents of which are incorporated herein in their entirety.

FIELD OF THE INVENTION

The invention relates to an endoprosthesis component with a body predefining the shape of the endoprosthesis component. On surface portions with which the endoprosthesis component in the implanted state is in contact with human tissue, the body is covered with an outer layer. The outer layer comprises a nitride, an oxynitride or an oxide based on a refractory metal; furthermore, the outer layer contains silver and/or copper. The invention further relates to a method for producing such an endoprosthesis component.

BACKGROUND OF THE INVENTION

Endoprosthesis components used to replace parts of the human skeleton must satisfy a number of requirements. The endoprosthesis component has to be sufficiently stable to ensure that it can take up the forces that occur in the skeleton. In addition, those elements of the endoprosthesis component that are in contact with the tissue, including bone substance, of the human body in the implanted state must have good biocompatibility.

It is already known for surface portions of the endoprosthesis component that are designed for contact with human tissue to be covered with a layer composed of a hard material, for example a nitride, an oxynitride or an oxide based on a refractory metal. Hard material coatings of this kind combine good mechanical properties together with good biocompatibility.

However, problems occasionally arise concerning the acceptance of such endoprosthesis components by the human body. For example, microorganisms may attach themselves to the surface of the endoprosthesis component and in so doing hinder the acceptance of the endoprosthesis component in the human body. The risk of microorganisms on the surface of endoprosthesis components is greater, the more invasive the procedure needed to implant the endoprosthesis component into the body, and the greater the surface area across which the endoprosthesis component comes into contact with the tissue of the body. Operations in which an invasive procedure is needed, and in which the endoprosthesis is brought into contact with human body tissue across a large surface area, are, for example, head/shaft prosthesis shafts, or those in which the femur is replaced completely by an endoprosthesis.

It is known from WO 03/094774 to oxidize the surface of an implant, made of metal or a metal alloy, and to provide the resulting hard material layer with silver particles in order to obtain an antimicrobial action. Since hard material layers react only very slowly with the surrounding body tissue, the silver particles are released from the hard material layer over a long period of time. A hard material coating of this kind can therefore provide good long-term action. Directly after insertion of the implant, however, a large number of microorganisms may be present in the environment of the implant. The quantity of silver particles released by the hard material layer is too small to be effective against a larger number of microorganisms.

SUMMARY OF THE INVENTION

The object of the invention is to make available an endoprosthesis component of the type mentioned at the outset and a method for producing such an endoprosthesis component, where there is less chance of the acceptance of the endoprosthesis component in the human body being hindered by microorganisms. The object is achieved by the features as broadly disclosed and advantageously in accordance with the detailed embodiments set forth below. The endoprosthesis component according to the invention is characterized in that an intermediate layer is provided between the outer layer and the body and in that parts of the intermediate layer are accessible from the outside.

A number of terms will first be explained.

A body that predefines the shape of the endoprosthesis component differs from the shape of the endoprosthesis component, at least in the area in which the surface of the endoprosthesis component is designed for contact with human tissue, only in terms of coatings that are additionally applied to the surface.

It is not generally the entire surface of the endoprosthesis component that is designed to establish a connection to human tissue. Instead, the endoprosthesis component can comprise areas on its surface that are designed to interact, for example, with a further endoprosthesis component, for example in order to form a joint. In the context of the invention, it is not necessary for the entire area of the surface designed for contact with the human tissue to be covered with an outer layer or an intermediate layer. Instead, it can suffice if surface portions of these areas are covered with an outer layer and/or an intermediate layer.

The outer layer is understood as a layer that is in direct contact with the environment. An outer layer, therefore, is not covered by a further layer. The outer layer does not have to provide full surface coverage; it can also have interruptions or can be applied only as islands.

An intermediate layer is covered at least on parts of its surface with an outer layer. In areas where no outer layer is applied or where the outer layer has interruptions, the intermediate layer itself is in direct contact with the environment. The intermediate layer is therefore partially accessible from the outside. On the surface of the endoprosthesis component, locations where the intermediate layer is accessible from the outside alternate with locations where the intermediate layer is not accessible from the outside. The intermediate layer is made of a different material than the material from which the endoprosthesis component is made.

The term human tissue is to be understood widely. It includes all elements of the human body with which an endoprosthesis can come into contact, for example including bone too.

Refractory metals are base metals with high melt points from the fourth, fifth and sixth side groups. These include titanium, zirconium and hafnium from the fourth side group, vanadium, niobium and tantalum from the fifth side group, and chromium, molybdenum and tungsten from the sixth side group. Refractory metals that are especially suitable for the coating of endoprosthesis components are titanium, zirconium, niobium and tantalum. Nitride, oxynitride or oxide based on a refractory metal are understood as compounds that ions of a refractory metal form with oxygen and/or nitrogen as reactive gas. These compounds are distinguished by great hardness; the layer obtained is therefore also referred to as hard material layer.

If the outer layer additionally comprises silver and/or copper, the formation of the nitride, oxynitride or oxide involves not only ions of the refractory metal and a reactive gas, but also silver and/or copper ions. The silver and/or copper ions are integrated into the coating obtained. The outer layer has a long-term antimicrobial action through the silver and/or copper contained. The antimicrobial action is combined with good mechanical properties such as hardness and high abrasion resistance.

By providing an intermediate layer between the outer layer and the body, which intermediate layer is partially accessible from the outside, it is possible for the surface of the endoprosthesis component not only to have the long-term antimicrobial action of the hard material coating, but also other effects. Thus, for example, the intermediate layer can be designed such that it releases a higher dose of an antimicrobial substance within a short time. The higher dose then acts against infections directly after the operation.

The body predefining the shape of the endoprosthesis component can be made of metal or of a metal alloy. Particularly suitable metals are titanium and titanium alloys. The term outer layer also includes a layer that has been created in several application runs. The application of a layer in several application runs will be considered particularly in cases where the layer created in one application run is too thin.

The intermediate layer can be a layer of silver, copper and/or gold. The intermediate layer preferably gives full surface coverage. Such an intermediate layer corrodes much more quickly than the hard material of the outer layer when in contact with human tissue. A higher dose of antimicrobial particles is therefore released.

In areas where the intermediate layer is accessible from the outside, the outer layer is interrupted. The interruptions can have diameters of just a few μm or can be much larger. In the case of microscopic interruptions with a minimum diameter of just a few μm, this is referred to as a porous outer layer. Macroscopic interruptions with diameters in the mm range, for example, permit access to the intermediate layer from the outside over a larger surface area. In particular, the outer layer can be designed such that the interruptions take up a proportion of at least 20% of the surface, preferably at least 40%, more preferably at least 60%.

The antimicrobial action can be strengthened if the outer layer has a microstructure or nanostructure with distinct peaks. A distinct peak in a surface structure is understood as a formation in which the surface, starting from one extreme, falls off in all directions at an angle of more than 45 degrees relative to the direction of the surface. Electrically conductive peaks, compared to smooth surfaces, generate a strong electric field in their environment, which field has a negative effect on microorganisms.

The invention further relates to a method for producing such an endoprosthesis component. To produce the endoprosthesis component, a body is first made ready that predefines the shape of the endoprosthesis component. Surface portions of the body that are intended for a connection to human tissue are provided with a coating which, although at this time not yet covered with an outer layer, will, however, be referred to as intermediate layer for the sake of simplicity. No particular requirements are placed on the surface structure of the intermediate layer. The surface can therefore be smooth, macro-structured, micro-structured or nanostructured.

Moreover, targets are made ready from which the material later to form the coating can be released. It is possible to make available a single target, which comprises both the refractory metal and also the silver and/or copper. It is also possible, however, to make available several targets, in which case a first target comprises a refractory metal, and a second target comprises silver and/or copper.

Ions of the refractory metal and ions of silver and/or copper are released from the one or more targets. In order to release the ions, for example, an electric arc can be generated between an electrode and the target, which electric arc delivers so much energy to the target that ions are released. Another possible way of delivering sufficient energy locally to the target can be to direct a laser beam at the target. One alternative, albeit an expensive one, is for the energy to be delivered by an electron beam.

The free ions are conducted, together with a reactive gas, onto surface portions of the body covered with the intermediate layer in such a way that an outer layer forms through which the intermediate layer is accessible. To do so, a voltage can be applied between the target and the body so as to accelerate the ions in the direction of the body. The reaction vessel with target and body contains a reactive gas, for example oxygen or nitrogen, or a mixture of oxygen and nitrogen. The ions of the refractory metal and the ions of silver and/or copper react with the reactive gas, and molecules are formed which contain all three constituents. In one embodiment, TiAgN molecules are formed. The outer layer according to the invention occurs as a result of the reaction taking place on the surface of the body. The reaction can take place under vacuum, preferably under high vacuum. Methods of this kind are referred to as plasma coating methods. An improved hold of an applied layer can be achieved if the surface of the body is treated beforehand by sand-blasting.

There are several options by means of which it can be ensured that the outer layer forms such that the intermediate layer remains accessible. For example, a porous outer layer having microscopic interruptions can be generated by delivering so much energy to the single target or the several targets that not only ions are released from the targets, but also fragments with a maximum diameter of over 20 μm. The fragments move randomly in all directions and impinge on that surface of the body on which the outer layer forms. At the locations where the fragments impinge, a piece of the forming outer layer is struck out. A porous outer layer forms through which the intermediate layer is accessible.

Another possible way of ensuring accessibility to the intermediate layer is to use a mask made of temperature-stable material to cover the surface portion of the body that is to be coated. The mask covers parts of the surface and leaves other parts of the surface free. The mask can, for example, have a mesh-like or lattice-like form. The outer layer then only forms as islands at the places that are left free by the mask. After the temperature-stable material has been removed, the intermediate layer is accessible in accordance with the mask. A material is referred to as being temperature-stable when it is resistant to the conditions that arise in plasma coating methods. The temperature-stable material can, in particular, be a metal.

If the parameters of the plasma coating method are suitably chosen, an outer layer is obtained that has a microstructure or nanostructure with distinct peaks.

If the intermediate layer is made of silver, copper and/or gold, it can likewise be applied by means of a plasma coating method. Alternatively, it is possible to apply the intermediate layer to the body by means of electrochemical deposition.

BRIEF DESCRIPTION OF THE DRAWINGS

The invention is described by way of example below on the basis of an advantageous embodiment and with reference to the attached drawings, in which.

DETAILED DESCRIPTION OF THE INVENTION

Figure 1:
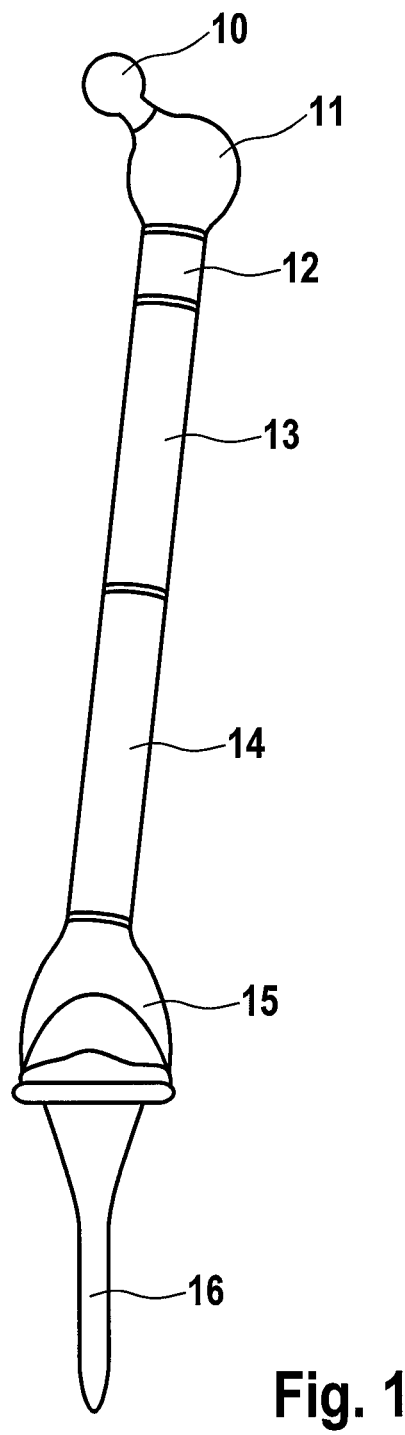
FIG. 1 shows an endoprosthesis comprising several endoprosthesis components.

An endoprosthesis shown in FIG. 1 is designed to replace a part of the human skeleton reaching from the hip to below the knee. A spherical joint head 10 forms an articulation surface that is designed to interact with an acetabulum. The joint head 10 is connected to a head piece 11 of the endoprosthesis by a screwed connection. The part of the endoprosthesis replacing the shaft of the femur comprises three endoprosthesis components 12, 13, 14. The endoprosthesis components 12, 13, 14 are connected to one another and also to the head piece 11 by screwed connections. A knee piece 15 forms an articular connection to a shaft 16, which is designed to connect the endoprosthesis to a tibia.

Figure 2:
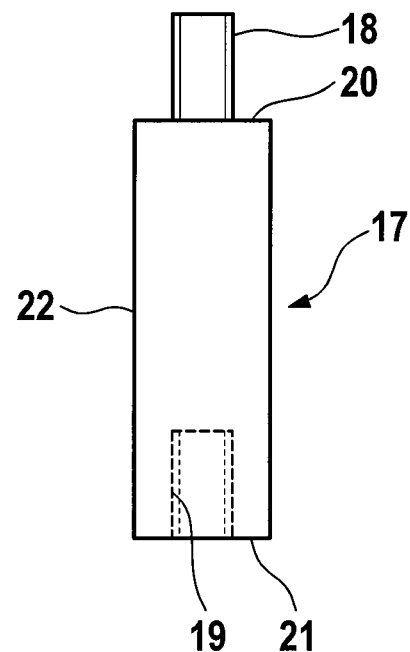
FIG. 2 shows an endoprosthesis component according to the invention.

The endoprosthesis components 12, 13, 14 are available in different lengths, such that the endoprosthesis can be adapted to different lengths of femurs. FIG. 2 shows an endoprosthesis component 17, corresponding to the endoprosthesis components 12, 13, 14, in an enlarged view. The endoprosthesis component 17 comprises a screw pin 18, and a screw hole 19 indicated by broken lines. By way of the screw pin 18 and the screw hole 19, the endoprosthesis component 17 can be connected at its two ends to similar endoprosthesis components, for example the endoprosthesis components 12, 13, 14. The screw pin 18, the screw hole 19 and the adjacent end faces 20 and 21 thus form areas of the surface of the endoprosthesis component 17 that are designed to interact with other endoprosthesis components. By contrast, the lateral surface 22 of the endoprosthesis component 17 is designed to make contact with human tissue in the implanted state.

In the area of the lateral surface 22, the body 23 predefining the shape of the endoprosthesis component 17 is covered with an intermediate layer 24 and an outer layer 25. The intermediate layer 24, composed of silver, completely covers the body 23 in the area of the lateral surface 22. The outer layer 25 covering the intermediate layer 24 is a hard material coating which was created by means of a plasma coating method from titanium, nitrogen and silver.

Figure 4:
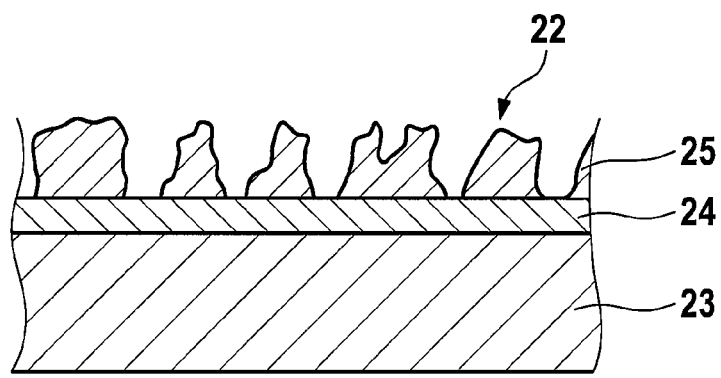
FIG. 4 shows the view from FIG. 3 in the case of another embodiment of the invention.

In the illustrative embodiment shown in FIG. 4, the outer layer 25 is porous. The intermediate layer 24 can exert an antimicrobial action on the surrounding tissue through microscopic interruptions in the outer layer 25.

Figure 3:
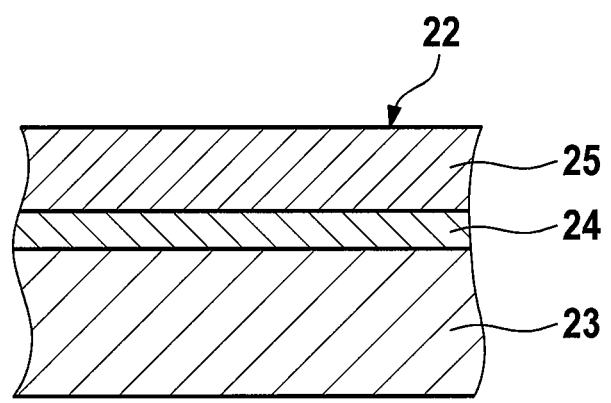
FIG. 3 shows an enlarged detail from a cross section through FIG. 2.
Figure 6:
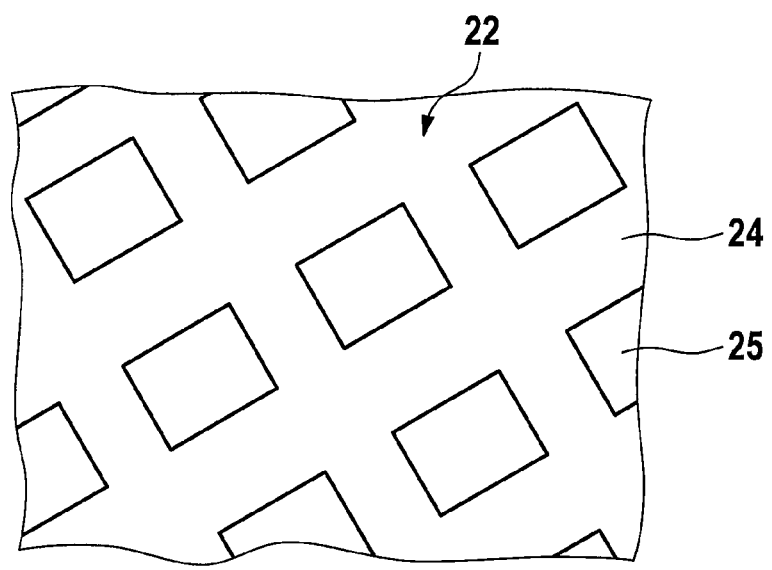
FIG. 6 shows an enlarged detail of the surface of the endoprosthesis component according to FIG. 2, in the case of one embodiment of the invention.

FIG. 6 shows a plan view of the lateral surface 22 of the endoprosthesis component 17 in an enlarged representation. The intermediate layer 24 is covered by the outer layer 25 only in individual islands. The outer layer 25 thus has macroscopic interruptions through which the surrounding tissue can come into direct contact with the intermediate layer 24. In the areas in which the outer layer 25 is applied to the intermediate layer 24, the intermediate layer 24 can be dense as shown in FIG. 3 so that no direct contact exists between the surrounding tissue and the intermediate layer 24.

Figure 5:
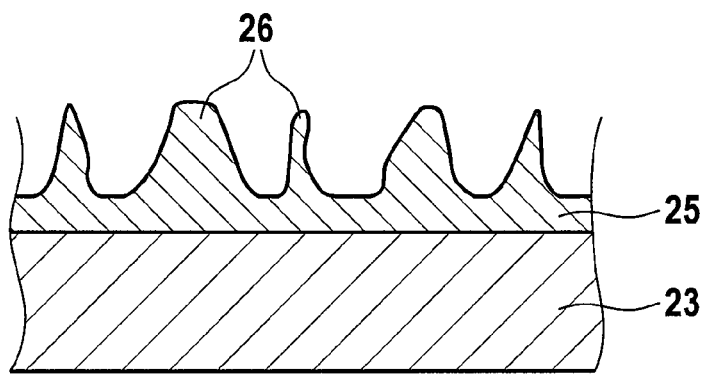
FIG. 5 shows the view from FIG. 3, in the case of a further embodiment of the invention.

In FIG. 5, the outer layer 25 has a nanostructure with pronounced peaks 26. With electrically conductive peaks 26, an electric field forms around the peaks 26 and strengthens the antimicrobial action of the outer layer 25. The intermediate layer is not shown in FIG. 5.

The invention claimed is:

1. An endoprosthesis component comprising:
    a body;
    an outer layer covering the body on surface portions configured to come into contact with human tissue in an implanted state, wherein the outer layer consists of: a) a nitride based on a refractory metal, an oxynitride based on a refractory metal or an oxide based on a refractory metal, and b) one or more of silver and copper; and
    an intermediate layer arranged between the outer layer and the body, wherein parts of the intermediate layer are accessible to the human tissue in the implanted state.

2. The endoprosthesis component of claim 1, wherein the intermediate layer is composed of one or more of silver, copper and gold.

3. The endoprosthesis component of claim 1 or 2, wherein the outer layer includes interruptions, and wherein the interruptions occupy a proportion of at least 20% of a surface area of the endoprosthesis component across which the endoprosthesis component is configured to come into contact with the human tissue.

4. The endoprosthesis component of claim 3, wherein the outer layer is porous.

5. The endoprosthesis component of claim 4, wherein the outer layer has a microstructure or nanostructure with distinct peaks.

6. A method for producing an endoprosthesis component, comprising:
    providing a body of the endoprosthesis component covered with an intermediate layer on surface portions of the body that are configured to come into contact with human tissue in an implanted state;
    providing a refractory metal and also one or more of silver and copper in the form of one or more targets;
    releasing ions of the refractory metal and also ions of the one or more of silver and copper from the one or more targets; and
    conducting the ions, together with a reactive gas comprising one or more of oxygen and nitrogen, onto the surface portions covered with the intermediate layer so that an outer layer forms the outer layer consisting of: a) a nitride based on the refractory metal, an oxynitride based on the refractory metal or an oxide based on the refractory metal, and b) the one or more of silver and copper, with the intermediate layer being accessible through said outer layer to the human tissue in the implanted state.

7. The method of claim 6, wherein the ions are released from the one or more targets by means of an electric arc.

8. The method of claim 7, wherein the intermediate layer includes one or more of silver, gold and copper.

9. The method of claim 6, wherein the ions are released from the one or more targets by means of a laser.

10. The method of claim 9, wherein the intermediate layer includes one or more of silver, gold and copper.

11. The method of claim 6, wherein the ions are released from the one or more targets by means of an electron beam.

12. The method of claim 11, further comprising
    releasing fragments with a diameter of more than 20 µm from the one or more targets, and
    conducting the fragments onto the body.

13. The method of claim 6, wherein, the intermediate layer includes one or more of silver, gold and copper.

14. The method of claim 13, further comprising prior to the step of conducting the ions, covering a surface portion of the body to be coated with a mask made of a temperature-stable material.

* * * * *